United States Patent [19]
Adesunloye et al.

[11] Patent Number: 5,874,106
[45] Date of Patent: *Feb. 23, 1999

[54] FILLED GELATIN CAPSULES

[75] Inventors: Adedotun Tony Adesunloye, Aurora; Paul Edward Stach, Broomfield, both of Colo.

[73] Assignee: Novartis Finance Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 812,232

[22] Filed: Mar. 6, 1997

Related U.S. Application Data

[60] Provisional application No. 60/013,289 Mar. 12, 1996.

[51] Int. Cl.$^6$ ........................................ A61K 9/48
[52] U.S. Cl. ........................ 424/456; 424/408; 514/962
[58] Field of Search ................................ 424/456, 408; 426/89; 574/962

[56] References Cited

U.S. PATENT DOCUMENTS

| | | |
|---|---|---|
| 2,467,715 | 4/1949 | White . |
| 2,519,487 | 8/1950 | Macek ..................... 424/456 |
| 4,255,413 | 3/1981 | Rattle et al. . |
| 5,186,944 | 2/1993 | Ishii et al. ............... 424/520 |
| 5,405,616 | 4/1995 | Wunderlich et al. ............ 424/451 |
| 5,620,704 | 4/1997 | Cade et al. ............... 424/456 |

FOREIGN PATENT DOCUMENTS

| | | |
|---|---|---|
| 2 617 047 | 12/1988 | France . |
| 225 426 A1 | 7/1985 | Germany . |

OTHER PUBLICATIONS

Patent Abstracts of Japan, vol. 8, No. 1261 (C–228)—13 Jun. 1984 of JP 57152080.
Patent Abstracts of Japan, vol. 13, No. 3 (C–557)—1 Jun. 1989 of JP63215641.
J.T. Carstensen & C.T. Rhodes; Drug Development & Industrial Pharmacy, 19(20), 2709–2712 (1993).
K.S. Murthy, R.G. Reisch, Jr., & M.B. Fawzi; Pharmaceutical Technology, 53–58, (Jun. 1989) pp. 53–56, 58.
K.S. Murthy, N.A. Enders, & M.B. Fawzi: Pharmaceutical Technology, 72–85 (Mar. 1989), pp. 72, 75–76, 78–79, 83–85.
L. Chafetz: Journal of Pharmaceutical Sciences, vol. 73, No. 8, (Aug. 1984) pp. 1186–1187.
G.A. Digenis, T.B. Gold & V.P. Shah; Journal of Pharmaceutical Sciences, vol. 83, No. 7, (Jul. 1994).
C.M. Marks, et al.; Food Technology, vol. 22, 1433, (Nov. 1968).

*Primary Examiner*—Neil S. Levy
*Attorney, Agent, or Firm*—George R. Dohmann

[57] ABSTRACT

Disclosed is a method of reducing crosslinking in gelatin capsules wherein an amino acid and a carboxylic acid are incorporated into the capsule fill, as well as filled gelatin capsules that utilize the disclosed method. The inventive method is especially useful for pharmaceutical formulations which include hydrochlorothiazide, triamterene, gemfibrozil, chloramphenicol, etodolac, piroxicam, nifedipine, tetracycline, diphenhydramine, hydroflumethiazide and rifampin, or a combination thereof as active ingredient.

18 Claims, No Drawings ns in the gelatin shell of a filled gelatin capsule by incor-
FILLED GELATIN CAPSULES This application claims the benefit under 35 U.S.C. 119(e) of U.S. Provisional Application Ser. No. 60/013,289, filed Mar. 12, 1996.

SUMMARY

This invention relates to a method of reducing crosslinking in the gelatin shell of a filled gelatin capsule by incorporating an amino acid and a carboxylic acid into the capsule filling. The inventive filled gelatin capsules possess improved stability relative to filled capsules which do not contain both the amino acid and the carboxylic acid in the filling.

BACKGROUND

The use of filled gelatin capsules as delivery devices is well-known in many art fields, especially the pharmaceutical sciences. In pharmaceutical applications, filled gelatin capsules are especially suitable as a means to orally administer a pharmaceutical product to a subject.

It is known that the presence of certain ingredients in the filling promote crosslinking in the gelatin shell with the passage of time and/or under stress conditions. When crosslinking occurs, the gelatin shell becomes less soluble in aqueous media, especially acidic aqueous media. Crosslinking causes retardation of the disintegration of the capsule shell, and thus retardation of the dissolution of the capsule contents, relative to identical capsules which have not been subjected to the passage of time or stress conditions. Thus, when a filled gelatin capsule contains an ingredient which promotes crosslinking in the gelatin shell, it is a challenge to prepare a formulation which does not show retarded disintegration and/or dissolution when the filled capsule is subjected to the passage of time and/or stress conditions.

It is likely that crosslinking has a much greater impact on the results of in vitro dissolution testing than on the in vivo bioavailability of drugs formulated in gelatin capsules. However, since in vitro dissolution testing is commonly employed as a method of measuring the stability of drug products, it is important to utilize a capsule fill which minimizes crosslinking in the capsule shell and thus minimizes the impact of time and/or stress conditions on the dissolution profile of the filled gelatin capsule, especially during accelerated stability studies wherein the capsules are subjected to high temperature and relative humidity.

The present invention relates to the discovery that the effects of crosslinking in a gelatin capsule which contains a material that promotes crosslinking are reduced or eliminated by incorporating an effective crosslinking-reducing amount of a combination of at least one amino acid and at least one carboxylic acid in the capsule fill. Both the amino acid and the carboxylic acid are required to obtain the beneficial effects of the present invention.

DETAILED DESCRIPTION

The present invention relates to a method of reducing crosslinking in a filled gelatin capsule, which filled gelatin capsule consists essentially of a gelatin shell and a filling which is encapsulated by the gelatin shell, wherein the filling comprises a material which promotes crosslinking in the gelatin shell, which method comprises incorporating into the filling an effective crosslinking-reducing amount of a combination of at least one amino acid, or salt thereof, and at least one monomeric carboxylic acid, or salt thereof, which is different from the amino acid and which is in addition to any stearic acid or salt thereof present in the filling; especially wherein the material which promotes crosslinking in the gelatin shell is a pharmaceutical active ingredient or a pharmaceutically acceptable excipient, or a combination thereof.

Filled gelatin capsules and their manufacture are well-known in the pharmaceutical arts. Filled gelatin capsules include any dosage form wherein a filling is encapsulated by a gelatin shell, for example, hard capsules wherein two partial capsule shells are interlocked to form the capsule shell, soft capsules wherein a filling is encapsulated by a one piece gelatin shell and caplets wherein a formed tablet is coated with a gelatin shell.

Crosslinking refers to crosslinking between the polypeptide chains of the gelatin shell.

Materials which promote crosslinking in the capsule shell include any material which promotes crosslinking between the polypeptide chains of the gelatin shell or slows dissolution with the passage of time and/or upon exposure to stress conditions such as high temperature and/or humidity. Materials which are especially prone to promote crosslinking include carbonyl compounds, such as ketones, aldehydes and derivatives thereof. Thus, the material which promotes crosslinking in the gelatin shell generally includes a carbonyl compound or a derivative thereof, or an ingredient which decomposes into a carbonyl compound or a derivative thereof. The carbonyl compound is especially an aldehyde. Thus, the material which promotes crosslinking in the gelatin shell is especially intended to include, but not be not limited to, aldehydes and/or materials which decompose into an aldehyde; in particular formaldehyde.

It is a routine matter to determine whether a material in the capsule filling is causing crosslinking in the capsule shell. For example, the capsule filling contains a material that promotes crosslinking if pellicle formation, and therefore slowed dissolution, is observed during accelerated stability studies, such as storage at 85 percent relative humidity and 40° C. for four weeks. In general, the term "slowed dissolution" is intended to mean that the average dissolution at 45 minutes is reduced by at least 20 percent after the capsules are subjected to the above accelerated stability study conditions. Alternatively, the presence of formaldehyde in the capsule after it is stored under the accelerated stability study conditions set forth above is also a clear indication that the filling contains a material which promotes crosslinking in the gelatin capsule shell.

An effective crosslinking-reducing amount is intended to mean an amount which is effective to maintain the dissolution at 45 minutes of capsules stored for four weeks under accelerated storage conditions within ±2% of an initial dissolution carried out prior to storage. Preferably, the dissolution of the stored capsules is within ±10% of the initial dissolution.

The material which promotes crosslinking in the gelatin shell is preferably a pharmaceutical active ingredient, a pharmaceutical excipient or a combination thereof.

Any pharmaceutical active ingredient suitable for administration by capsule is suitable for use in the capsules stabilized by the present method. However, the present method is especially suitable for stabilizing capsules which contain a pharmaceutically effective amount of an active ingredient which promotes crosslinking in the capsule shell. Such pharmaceutically active ingredients include hydrochlorothiazide, triamterene, gemfibrozil, chloramphenicol, etodolac, piroxicam, nifedipine, tetracycline, diphenhydramine, hydroflumethiazide and rifampin, or a combination thereof. The above description is intended to include all salt forms of the pharmaceutical active ingredient.

Pharmaceutically acceptable excipients are well-known in the pharmaceutical sciences. Acceptable pharmaceutical excipients include those described in the *Handbook of Pharmaceutical Excipients,* which is published by the American Pharmaceutical Association, Washington D.C.. Especially useful pharmaceutically acceptable excipients include monosaccharides, such as glucose and fructose, disaccharides, such as lactose and sucrose, trisaccharides, such as raffinose, polysaccharides, such as starches like corn starch and potato starch and starch derivatives like sodium starch glycolate or pregelatinized starch, surfactants, especially nonionic surfactants such as ethoxylated sorbitan or polysorbate 80, lubricants, such as magnesium stearate, sodium stearyl fumarate or hydrogenated vegetable oil, disintegrants, such as cross-linked povidone, binders, such as povidone, and pharmaceutically acceptable dyes and pigments, such as FD&C Red #3.

Preferably, the material which promotes crosslinking in the gelatin shell is a combination of a pharmaceutical active ingredient and at least one pharmaceutically acceptable excipient.

Preferably, the filling comprises from about 0.1 to about 25 percent by weight of the amino acid and from about 0.01 to about 10 percent by weight of the carboxylic acid, most preferably from 1 to 5 percent by weight of the amino acid and from 0.1 to 1 percent by weight of the carboxylic acid, the percentage by weight being based on the weight of the capsule fill.

The amino acid is believed to function by acting as a carbonyl scavenger, especially a formaldehyde scavenger, although the ability of an amino acid to function as both an acid and a base may also contribute to its utility. The carboxylic acid is believed to facilitate the complete solubility of the amino acid in water and to stabilize the pH of the capsule fill.

Amino acids are well-known in the art. Useful amino acids include compounds which contain both a free carboxylic acid group and an amino group, especially a primary amino group, or salt forms thereof, including monomer amino acids and short peptide chains, especially those which are composed of two or three amino acid residues. Monomer amino acids, such as alpha and omega amino acids are especially useful. Amino acids which are the building blocks of proteins in plants and in particular mammals are especially useful. The most useful amino acids are those selected from the group consisting of glycine, tryptophan, lysine, leucine, threonine, aspartic acid, glutamic acid, asparagine, glutamine, lysine, arginine, cysteine, phenylalanine, tyrosine, histidine, acetylcysteine, valine, alanine, isoleucine, ornithine, p-aminobenzoic acid, and nicotinic acid. Glycine is an especially useful amino acid. The carboxylic acids and salts useful in the present method are monomeric carboxylic acids and salts, but not stearic acid and its salts, for example, magnesium or calcium stearate. Polymeric carboxylic acids and their salts, such as sodium starch glycolate, are not within the scope of the carboxylic acids that are used according to the present invention.

Carboxylic acids and salts which are especially useful in the present method are monomeric C4-C20 carboxylic acids containing one, two or three —COOH groups, especially two or three —COOH groups, or a salt thereof. Preferably, the monomeric carboxylic acid is a C4-C10 carboxylic acid, or salt thereof. It is preferred to use a carboxylic acid. Especially useful carboxylic acids and salts are those selected from the group consisting of benzoic acid, fumaric acid, maleic acid, citric acid, ascorbic acid, edetic acid, lactic acid, sorbic acid, tartaric acid, adipic acid, succinic acid, and gluconic acid, or a salt thereof. Citric acid is an especially useful carboxylic acid. Preferably, the carboxylic acid or salt is water-soluble.

Useful salts include those containing any pharmaceutically acceptable cation, especially alkali metal, alkaline earth metal and ammonium salts.

It is possible for an acidic amino acid, such as glutamic or aspartic acid, to function as either the amino acid or the carboxylic acid. However, the amino acid and the carboxylic acid used in the capsule fill cannot be the same compound, or a salt of the same compound.

The present method especially relates to filled gelatin capsules wherein the filling comprises a combination of triamterene and hydrochlorothiazide as pharmaceutically active ingredient, especially wherein glycine is the amino acid and citric acid is the carboxylic acid; for example those wherein the filling comprises from 10 to 100 mg of triamterene and from 10 to 100 mg of hydrochlorothiazide per capsule, glycine is the amino acid and citric acid is the carboxylic acid.

In another aspect, the present invention relates to filled gelatin capsules which are stabilized by the inventive methods. Accordingly, the present invention relates to a filled gelatin capsule which consists essentially of a gelatin shell and a filling which is encapsulated by the gelatin shell, wherein the filling comprises a material which promotes crosslinking in the gelatin shell and an effective crosslinking-reducing amount of a combination of at least one amino acid, or salt thereof, and at least one monomeric carboxylic acid, or salt thereof, which is different from the amino acid and which is in addition to any stearic acid or salt thereof present in the filling.

The materials and preferences discussed above relating to the inventive method also apply to the inventive filled gelatin capsules.

Thus, the present invention relates to the filled gelatin capsules described above wherein the material which promotes crosslinking in the gelatin shell is a pharmaceutical active ingredient or a pharmaceutically acceptable excipient, or a combination thereof; especially wherein the pharmaceutical active ingredient is a pharmaceutically effective amount of a compound selected from the group consisting of hydrochlorothiazide, triamterene, gemfibrozil, chloramphenicol, etodolac, piroxicam, nifedipine, tetracycline, diphenhydramine, hydroflumethiazide and rifampin, or a combination thereof and/or the pharmaceutically acceptable excipient is a monosaccharide, a disaccharide, a trisaccharide, a polysaccharide or a surfactant. Preferably, the material which promotes crosslinking in the gelatin shell is a combination of a pharmaceutical active ingredient and a pharmaceutically acceptable excipient.

Preferred amino acids used in the filled gelatin capsules include glycine, tryptophan, lysine, leucine, threonine, aspartic acid, glutamic acid, asparagine, glutamine, lysine, arginine, cysteine, phenylalanine, tyrosine, histidine, acetylcysteine, valine, alanine, isoleucine, ornithine and p-aminobenzoic acid; including salt forms thereof.

Preferred carboxylic acids and salts used in the filled gelatin capsules include C4-C20 carboxylic acids containing one, two or three —COOH groups, especially two or three —COOH groups, or salts thereof. Especially useful carboxylic acids include benzoic acid, fumaric acid, maleic acid, citric acid, ascorbic acid, edetic acid, lactic acid, sorbic acid, tartaric acid, adipic acid, succinic acid, and gluconic acid, or a salt thereof.

Preferably, the filling contains from about 0.1 to about 25 percent by weight of the amino acid and from about 0.01 to about 10 percent by weight of the carboxylic acid or salt. Most preferably, the filling contains from 1 to 5 percent by weight of the amino acid and from 0.1 to 1 percent by weight of the carboxylic acid or salt.

An advantage of the inventive filled gelatin capsules is that the dissolution profile remains stable during accelerated stability studies. In particular, the present invention relates to a filled gelatin capsule as described above wherein the dissolution profile at 45 minutes of capsules maintained at about 40° C. and 85 percent relative humidity for four weeks remains within ±10 percent of the initial dissolution of the capsules at 45 minutes and/or the dissolution profile at 45 minutes of capsules maintained at about 40° C. and 85 percent relative humidity for twelve weeks remains within 20 percent, preferably ±10 percent, of the initial dissolution of the capsules at 45 minutes. The initial and later dissolution profiles are measured under the same conditions except that the capsules used to measure the initial dissolution are not subjected to accelerated stability conditions.

Thus, the present invention further relates to a method of preparing a filled gelatin capsule wherein the dissolution profile at 45 minutes of capsules maintained at about 40° C. and 85 percent relative humidity for four weeks remains within ±10 percent of the initial dissolution of the capsules at 45 minutes and/or the dissolution profile at 45 minutes of capsules maintained at about 40° C. and 85 percent relative humidity for twelve weeks remains within 20 percent, preferably ±10 percent, of the initial dissolution of the capsules at 45 minutes, which comprises incorporating into the filled gelatin capsule an effective stabilizing amount of a combination of at least one amino acid, or salt thereof, and at least one monomeric carboxylic acid, or salt thereof, which is different from the amino acid and which is in addition to any stearic acid or salt thereof present in the filling. The materials and preferences discussed above for the filled gelatin capsules also applies to the inventive method of preparing a filled gelatin capsule; the stabilizing amount corresponding to the crosslinking-reducing amounts. The present invention further relates to filled gelatin capsules produced according to this method.

This aspect of the invention especially relates to filled gelatin capsules as described above wherein the filling contains from 10 to 100 mg of triamterene and from 10 to 100 mg of hydrochlorothiazide per capsule; especially wherein glycine is the amino acid and citric acid is the carboxylic acid, especially those which contain from 1 to 5 percent of the glycine and 0.1 to 1 percent of the citric acid, in particular, such capsules which have a dissolution profile in U.S.P. Apparatus No. 1 (baskets) at 100 r.p.m. in 900 ml. of 0.1N hydrochloric acid wherein at least 85 percent of both the triamterene and hydrochlorothiazide is dissolved within 45 minutes after the capsules are maintained at about 40° C. and 85 percent relative humidity for four weeks and/or wherein at least 80 percent of both the triamterene and hydrochlorothiazide is dissolved within 45 minutes after the capsules are maintained at about 40° C. and 85 percent relative humidity for eight weeks and/or wherein at least 80 percent of both the triamterene and hydrochlorothiazide is dissoluted within 45 minutes after the capsules are maintained at about 40° C. and 85 percent relative humidity for twelve weeks.

The present invention further relates to a filled gelatin capsule which comprises from 10 to 100 mg of triamterene and from 10 to 100 mg of hydrochlorothiazide per capsule wherein the dissolution profile of the filled gelatin capsule using U.S.P. Apparatus No. 1 at 100 r.p.m. in 900 ml. of 0.1N hydrochloric acid is at least 75 percent after 15 minutes for both the triamterene and hydrochlorothiazide after being maintained at about 40° C. and 85 percent relative humidity for twelve weeks.

The present invention further relates to a filled gelatin capsule which comprises a pharmaceutically effective amount of a pharmaceutical active ingredient, from 0.1 to 25 percent, preferably 1 to 5 percent, by weight of an amino acid, or salt thereof, and from 0.01 to 10 percent, preferably 0.1 to 1 percent, by weight of a monomeric carboxylic acid, or salt thereof, which is different from the amino acid and which is in addition to any stearic acid or salt thereof present in the filling, especially wherein the carboxylic acid is C4-C20 carboxylic acid with two or three —COOH groups, or a salt thereof.

Pellicle formation due to crosslinking is also promoted by placing a gelatin capsule in contact with certain packaging materials, for example rayon. According to the present invention, it is also possible to reduce or prevent crosslinking in the capsule shell that is promoted by a packaging material which is in contact with the gelatin capsule. Thus, the present invention further relates to a method of reducing crosslinking in a gelatin capsule, which gelatin capsule is in contact with a material that promotes crosslinking in the gelatin capsule, which method comprises incorporating into the gelatin capsule an effective crosslinking-reducing amount of a combination of at least one amino acid, or salt thereof, and at least one monomeric carboxylic acid, or salt thereof, which is different from the amino acid and which is in addition to any stearic acid or salt thereof present in the filling.

The following examples illustrate, but do not limit, the present invention. All percentages are by weight unless otherwise indicated.

EXAMPLE 1

Filled gelatin capsules containing each of the formulations described in Table 1 are prepared by granulating first with a glycine/citric acid solution in H2O followed by a solution of polysorbate 80 in isopropyl alcohol and then additional isopropyl alcohol until no dry powder remains and granules are formed. The wet granules are tray-dried in an oven and then milled. The milled product is transferred to a twinshell blender and blended and lubricated with magnesium stearate. The final blend is encapsulated with a #4 hard gel capsule.

TABLE 1

| | Formulas (% w/w) | | | |
|---|---|---|---|---|
| Ingredient | I | II | III | IV |
| Triamterene | 23.01 | 23.01 | 23.01 | 23.01 |
| Hydrochlorothiazide | 15.34 | 15.34 | 15.34 | 15.34 |
| Glycine | — | 2.50 | — | 2.50 |
| Citric acid | — | — | 0.50 | 0.50 |
| Others | 61.65 | 59.15 | 61.15 | 58.65 |

EXAMPLE 2

The filled capsules prepared according to Example 1 are stored at 40° C. and 85% relative humidity for the period of time indicated in Table 2. The dissolution profile is then measured using U.S.P. apparatus #1 at 100 rpm in 900 ml. of 0.1N hydrochloric acid in accordance with U.S.P. General Chapter <711> United States Pharmacopeia XXIII (1995). The dissolution profiles of the formulations prepared according to Example 1 are set forth in Table 2 (triamterene) and Table 3 (hydrochlorothiazide). Each dissolution profile represents the average dissolution rate of 6 capsules.

TABLE 2

Triamterene/Hydrochloride Capsules: Accelerated Stability at 40° C./85% RH
Triamterene Dissolution Profile at 15, 30, 45, and 60 minutes

| Formula | I | | | | II | | | | III | | | | IV | | | |
|---|---|---|---|---|---|---|---|---|---|---|---|---|---|---|---|---|
| Time(mins) | 15 | 30 | 45 | 60 | 15 | 30 | 45 | 60 | 15 | 30 | 45 | 60 | 15 | 30 | 45 | 60 |
| Initial | 78 | 88 | 93 | 95 | 69 | 83 | 88 | 91 | 92 | 104 | 107 | 109 | 84 | 94 | 96 | 97 |
| 4 - week | 5 | 10 | 13 | 16 | 21 | 40 | 50 | 57 | 4 | 14 | 27 | 38 | 85 | 95 | 97 | 98 |
| 8 - week | | | | | | | | | | | | | 84 | 94 | 97 | 98 |
| 12 - week | | | | | | | | | | | | | 82 | 93 | 96 | 97 |

TABLE 3

Triamterene/Hydrochlorothiazide Capsules: Accelerated Stability at 40° C./85% RH
Hydrochlorothiazide Dissolution Profile at 15, 30, 45 and 60 minutes

| Formula | I | | | | II | | | | III | | | | IV | | | |
|---|---|---|---|---|---|---|---|---|---|---|---|---|---|---|---|---|
| Time(mins) | 15 | 30 | 45 | 60 | 15 | 30 | 45 | 60 | 15 | 30 | 45 | 60 | 15 | 30 | 45 | 60 |
| Initial | 76 | 88 | 92 | 94 | 69 | 82 | 87 | 90 | 88 | 101 | 105 | 106 | 84 | 95 | 95 | 96 |
| 4 - week | 7 | 13 | 17 | 21 | 24 | 42 | 54 | 61 | 4 | 17 | 31 | 44 | 83 | 94 | 96 | 97 |
| 8 - week | | | | | | | | | | | | | 81 | 91 | 94 | 95 |
| 12 - week | | | | | | | | | | | | | 82 | 93 | 96 | 97 |

Formaldehyde is detectable by high pressure liquid chromatography in all formulations at all stability time points recorded in Tables 2 and 3.

EXAMPLE 3

The piroxicam and gemfibrozil capsule formulations described in Table 4 are prepared by an aqueous wet granulation process whereby the respective active ingredient, lactose, corn starch, sodium starch glycolate, colloidal silicon dioxide and povidone are mixed and subsequently granulated with polysorbate dissolved in purified water. Additional purified water is then added until granules form and no dry powder remains. Where applicable, glycine and citric acid are dissolved in the additional purified water. Wet granules are dried at 110° F. until loss on drying is not more than 2 percent. The dried granules are milled with the sodium starch glycolate, blended and lubricated with screened magnesium stearate in a twinshell blender. Formulations A and B are encapsulated in size 2 capsules, and Formulations C and D are encapsulated in size 0 capsules. The capsules are then stored in a HDPE plastic bottle and placed on accelerated stability stations at 40° C. and 85% relative humidity for a 12-week study.

TABLE 4

| Ingredients | A | B | C | D |
|---|---|---|---|---|
| Piroxicam | 50.0 | 50.0 | — | — |
| Gemfibrozil | — | — | 100.0 | 100.0 |
| Lactose, anhydrous | 124.4 | 124.4 | 248.8 | 233.8 |
| Corn starch | 50.0 | 50.0 | 100.0 | 100.0 |
| Sodium starch glycolate | 12.5 | 12.5 | 25.0 | 25.0 |
| Povidone | 2.5 | 2.5 | 5.0 | 5.0 |
| Polysorbate 80 | 7.5 | 7.5 | 15.0 | 15.0 |
| Colloidal silicon dioxide | 0.625 | 0.625 | 1.25 | 1.25 |
| Glycine | — | 6.25 | — | 12.5 |
| Citric acid | — | 1.25 | — | 2.5 |
| Magnesium stearate | 2.5 | 2.5 | 5.0 | 5.0 |
| TOTAL (mg) | 250 | 250 | 500 | 500 |

Physical disintegration testing of the piroxicam and gemfibrozil capsules is performed at an initial time point and at the 4 week, 8 week and 12 week intervals in a U.S.P. Apparatus 2 (paddle) with six replications by sinking the capsule in 900 ml of purified water at 37+/−1° C. with a paddle speed of 100 rpm.

Piroxicam capsules without glycine/citric acid (Formulation A) show an increase in disintegration time throughout the 12-week accelerated stability study. Disintegration increased from four minutes at the initial time point to twelve and fourteen minutes after 4- weeks and 8-weeks of accelerated study conditions, respectively. In contrast, disintegration time consistently remains between four and six minutes for all tested capsules at all tested stability time points for piroxicam capsules with glycine/citric acid (Formulation B).

Similar results are observed for the gemfibrozil capsules. Gemfibrozil capsules without glycine/citric acid (Formulation C), show an increase in disintegration time, going from nine minutes at the initial time point to twenty-two minutes after a 4-weeks, twenty-seven minutes at the 8-week point and forty-five minutes after 12 weeks at accelerated stability conditions. In contrast, disintegration time remains at about nine minutes at all tested intervals throughout the study for the gemfibrozil capsules with glycine/citric acid (Formulation D).

We claim:

1. A method of preparing a filled gelatin capsule wherein the dissolution profile at 45 minutes of capsules maintained at about 40° C. and 85 percent relative humidity for four weeks remains within ±10 percent of the initial dissolition of the capsules at 45 minutes and/or the dissolution profile at 45 minutes of capsules maintained at about 40° C. and 85 percent relative humidity for twelve weeks remains within ±20 percent of the initial dissolution of the capsules at 45 minutes, which comprises incorporating into the filled gelatin capsule a material which promotes crosslinking in the gelatin capsule and from 0.1 to 25 percent by weight of at least one monomeric amino acid, or salt thereof, and from 0.01 to about 10 percent by weight of at least one monomeric carboxylic acid, or salt thereof, which is different from the amino acid and which is in addition to any stearic acid or salt thereof present in the filling.

2. A method of claim 1 wherein the material which promotes crosslinking in the gelatin shell is a pharmaceutical active ingredient or a combination of a pharmaceutical active ingredient and a pharmaceutically acceptable excipient.

3. A method of claim 2 wherein the pharmaceutical active ingredient is a pharmaceutically effective amount of a compound selected from the group consisting of hydrochlorothiazide, triamterene, gemfibrozil, chloramphenicol, etodolac, piroxicam, nifedipine, tetracycline, diphenhydramine, hydroflumethiazide and rifampin, or a combination thereof.

4. A method of claim 3 wherein the filling comprises a combination of triamterene and hydrochlorothiazide as the pharmaceutical active ingredient.

5. A method of claim 4 wherein the filling comprises from 1 to 5 percent by weight of the amino acid or salt thereof, and from 0.1 to 1 percent by weight of the carboxylic acid or salt thereof.

6. A method of claim 2 wherein the carboxylic acid is a C4-C20 carboxylic acid with two or three -COOH groups or a salt thereof.

7. A method of claim 2 wherein the amino acid is selected from the group consisting of glycine, tryptophan, lysine, leucine, threonine, aspartic acid, glutamic acid, asparagine, glutamine, lysine, arginine, cysteine, phenylalanine, tyrosine, histidine, acetylcysteine, valine, alanine, isoleucine, ornithine, p-aminobenzoic acid and nicotinic acid, or a salt thereof, and the carboxylic acid is selected from the group consisting of benzoic acid, fumaric acid, maleic acid, citric acid, ascorbic acid, edetic acid, lactic acid, sorbic acid, tartaric acid, adipic acid, succinic acid and gluconic acid, or a salt thereof.

8. A method of claim 4 wherein the amino acid is glycine and the carboxylic acid is citric acid.

9. method of claim 4 wherein the amino acid is selected from the group consisting of glycine. tryptophan, lysine, leucine, threonine, aspartic acid, glutamic acid, asparagine, glutamine, lysine, arginine, cysteine, phenylalanine, tyrosine, histidine, acetylcysteine, valine, alanine, isoleucine, ornithine, p-aminobenzoic acid and nicotinic acid, or a salt thereof.

10. A method of claim 9 wherein the carboxylic acid is a C4-C20 carboxylic acid with two or three -COOH groups, or a salt thereof.

11. A method of claim 10 wherein the filling comprises from 10 to 100 mg of triamterene and from 10 to 100 mg of hydrochlorothiazide per capsule as the pharmaceutical active ingredient.

12. A method of claim 11 wherein the carboxylic acid is selected from the group consisting of benzoic acid, fumaric acid, maleic acid, citric acid, ascorbic acid, edetic acid, lactic acid, sorbic acid, tartaric acid, adipic acid, succinic acid and gluconic acid, or a salt thereof.

13. A method of claim 11 wherein the amino acid is glycine and the carboxylic acid is citric acid.

14. A method of claim 11 wherein the filling comprises from 1 to 5 percent by weight of the amino acid or salt thereof and from 0.1 to 1 percent by weight of the carboxylic acid or salt thereof.

15. A method of claim 11 for preparing a filled gelatin capsule having a dissolution profile in U.S.P. Apparatus No. 1 at 100 r.p.m. in 900 ml. of 0.1 N hydrochloric acid wherein at least 85 percent of both the triamterene and hydrochlorothiazide is dissoluted within 45 minutes after being maintained at about 40C and 85 percent relative humidity for four weeks.

16. A method claim 15 wherein the dissolution profile using U.S.P. Apparatus No. 1 at 100 r.p.m. in 900 ml. of 0.1N hydrochloric acid is at least 80 percent within 45 minutes for both the triamterene and hydrochlorothiazide after being maintained at about 40° C and 85 percent relative humidity for eight weeks.

17. A method of claim 16 wherein the dissolution profile using U.S.P. Apparatus No- 1 at 100 r.p.m. in 900 ml. of 0.1w hydrochloric acid is at least 80 percent after 45 minutes for both the triamterene and hydrochlorothiazide after being maintained at about 40 ° C and 85 percent relative humidity for-twelve weeks.

18. A method of claim 4 wherein the filling comprises from I 0 to 100 mg of triamterene and from 10 to 100 mg of hydrochlorothiazide per capsule and wherein the dissolution profile using U.S.P. Apparatus No. 1 at 100 r.p.m. in 900 ml. of 0.1 N hydrochloric acid is at least 75 percent after 15 minutes for both the triamterene and hydrochlorothiazide after being maintained at about 40° C-and 85 percent relative humidity for twelve weeks.

* * * * *